US00PP34684P2

(12) United States Plant Patent
Suiker

(10) Patent No.: US PP34,684 P2
(45) Date of Patent: Oct. 25, 2022

(54) ***FRAGARIA* PLANT NAMED 'FLORICE'**

(50) Latin Name: ***Fragaria* x *ananassa***
Varietal Denomination: Florice

(71) Applicant: Flevo Berry Holding B. V., Ens (NL)

(72) Inventor: Marcel Suiker, Vollenhove (NL)

(73) Assignee: Flevo Berry Holding B. V., Ens (NL)

( * ) Notice: Subject to any disclaimer, the term of this patent is extended or adjusted under 35 U.S.C. 154(b) by 0 days.

(21) Appl. No.: 17/803,155

(22) Filed: Mar. 8, 2022

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208, 209
See application file for complete search history.

(56) References Cited

PUBLICATIONS

UOPV—International Union for the Protectionof New Varieties of Plants; UPOV/INF/6/5 Apr. 6, 2017 (4 pages total.*

* cited by examiner

*Primary Examiner* — Susan McCormick Ewoldt
(74) *Attorney, Agent, or Firm* — Samuel R. McCoy, Jr.

(57) ABSTRACT

A new and distinct *Fragaria* x *ananassa* plant named 'Florice' which is characterized by the combination good disease resistance, good fruit set, an abundance of short conical, glossy red berries with firm flesh and a pleasant, sweet yet slightly acidic flavor, and the stability of these characteristics from generation to generation.

4 Drawing Sheets

Latin name of the genus and species: The Latin name of the genus and species of the novel variety disclosed herein is *Fragaria* x *ananassa*.

Variety denomination: The inventive cultivar of *Fragaria* disclosed herein has been given the variety denomination 'Florice'.

BACKGROUND OF THE INVENTION

Parentage: 'Florice' is a seedling selection that resulted from a controlled pollination breeding program carried out in April on 2013 in Ens, Netherlands. The new variety originated as a seedling from the crossing of *Fragaria* x *ananassa* '06-095-06' (unpatented), the seed parent, with *Fragaria* x *ananassa* '00-113-13' (unpatented) as the pollen parent. Seed from said cross was harvested, then germinated, and the resulting seedlings were grown to a mature size in order to evaluate for desirable commercial characteristics. In August of 2014, the inventor first observed the claimed *Fragaria*. The claimed plant was then subjected to a series of trials from 2014 through 2021 to evaluate the distinctness and stability of the characteristics first observed. In 2021, the claimed plant was finally selected as a new and distinctive cultivar.

Asexual Reproduction: Asexual reproduction of 'Florice', by way of rooting stolon cuttings, was first performed in September of 2014 in Ens, Netherlands. Through eight subsequent generations, the unique features of this cultivar have proven to be stable and true to type.

SUMMARY OF THE INVENTION

The cultivar 'Florice' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Florice'. These characteristics in combination distinguish 'Florice' as a new and distinct *Fragaria* cultivar:

1. *Fragaria* 'Florice' exhibits moderately dense foliage and a relative abundance of stolons; and
2. *Fragaria* 'Florice' exhibits good disease resistance; and
3. *Fragaria* 'Florice' exhibits good fruit set with an abundance of berries which maintain fruit size throughout the harvest season; and
4. *Fragaria* 'Florice' exhibits short conical, glossy red berries; and
5. *Fragaria* 'Florice' exhibits berries with firm flesh and a pleasant, sweet yet slightly acidic flavor.

BOTANICAL DESCRIPTION OF THE PLANT

Figure 1:
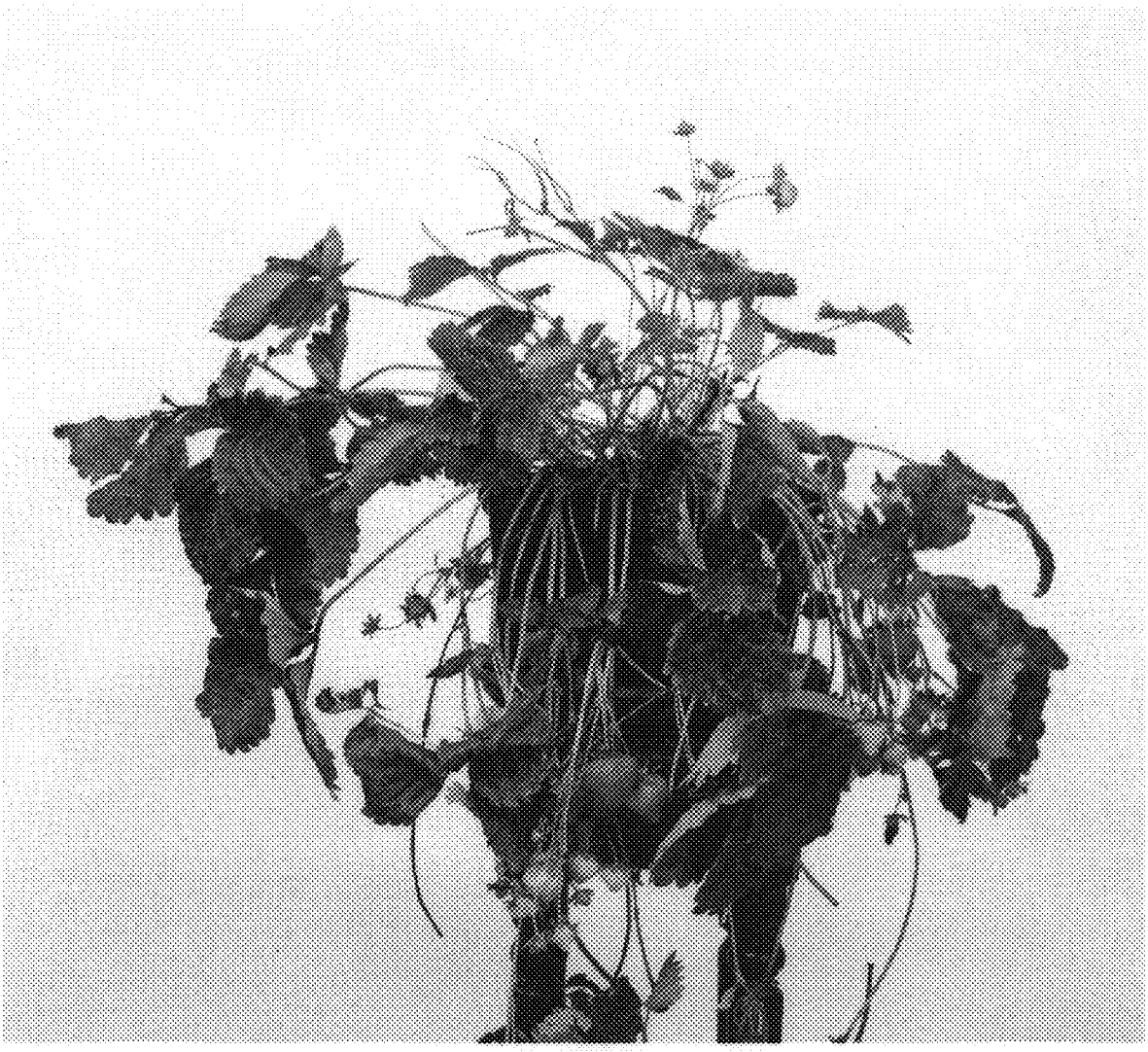
FIG. 1 illustrates, as nearly true as it is reasonably possible to make the same in color photographs of this type, an exemplary 12-month-old 'Florice' plant, grown at a commercial greenhouse in Ens, Netherlands.
Figure 2:
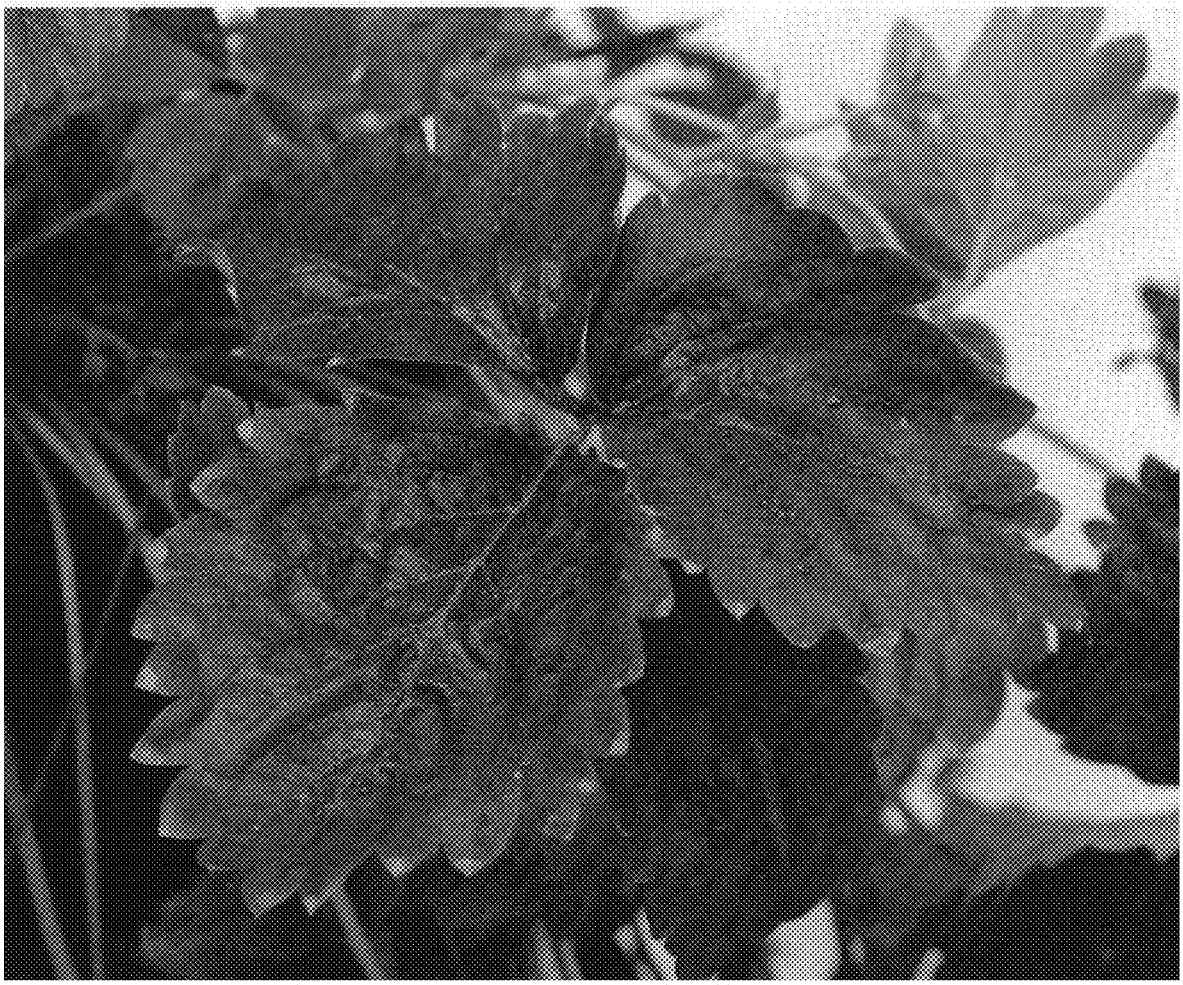
FIG. 2 illustrates, as nearly true as it is reasonably possible to make the same in color photographs of this type, the typical foliage of 'Florice'.
Figure 3:
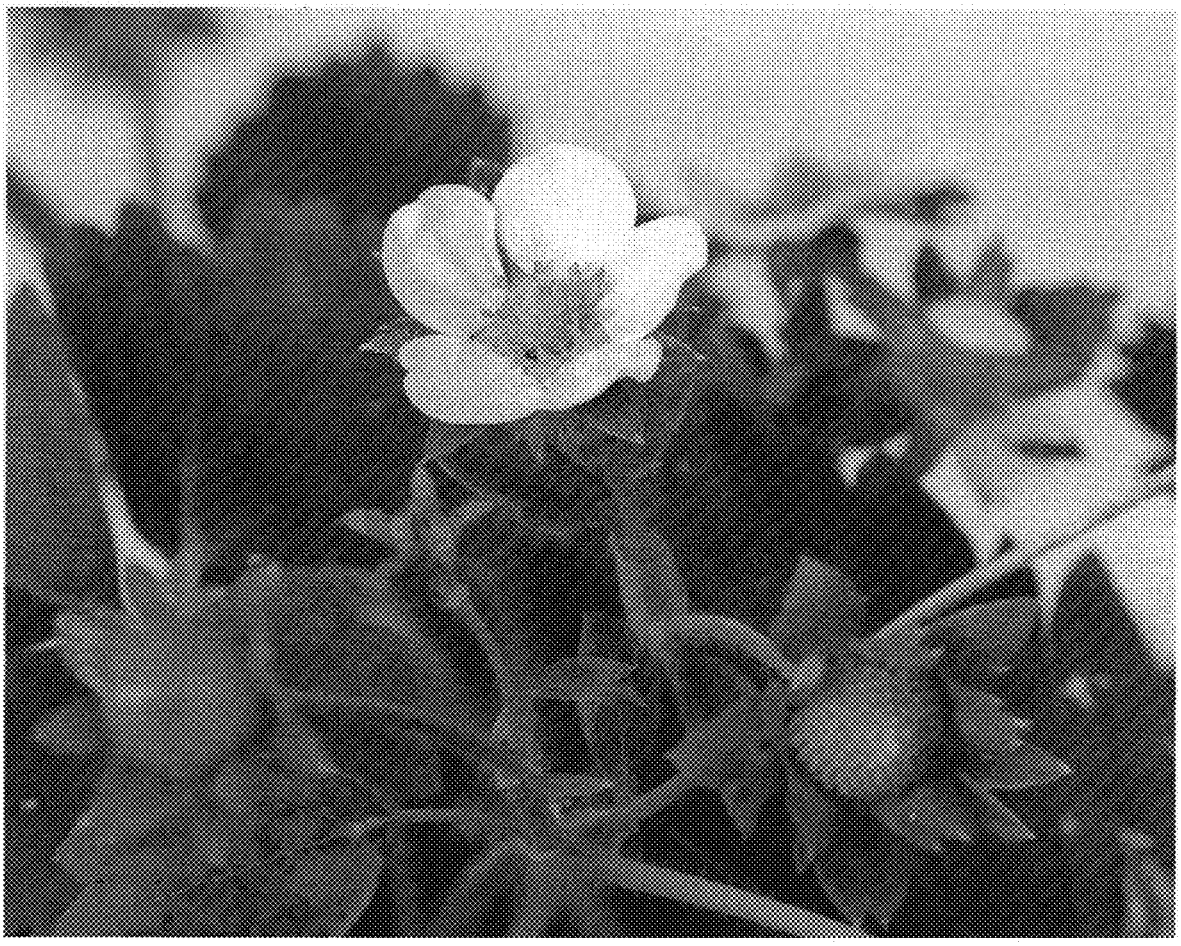
FIG. 3 illustrates, as nearly true as it is reasonably possible to make the same in color photographs of this type, the typical flower of 'Florice'.
Figure 4:
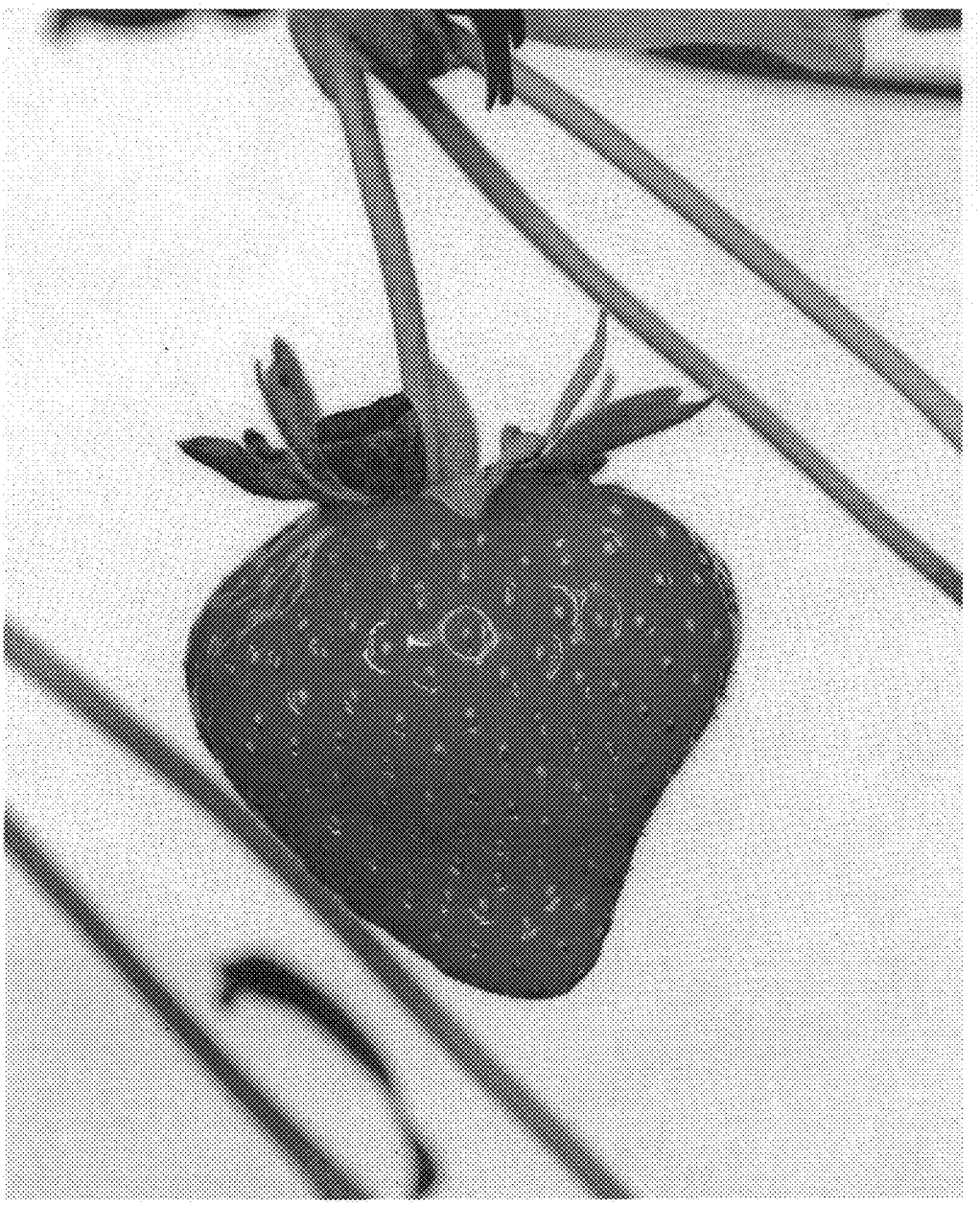
FIG. 4 illustrates, as nearly true as it is reasonably possible to make the same in color photographs of this type, the typical fruit of 'Florice'.

The following is a detailed botanical description of a new and distinct variety of *Fragaria* known as 'Florice', based upon observations of 12-month-old greenhouse-grown plants in 19 cm nursery containers, produced in Ens, Netherlands. Plants were grown on benches in a non-climate-controlled greenhouse, using conventional production protocols for *Fragaria* plants which consisted of drip irrigation with fertigation applications as needed. Biological insect control measures were utilized in production. Plants were produced with full sun exposure and no photoperiodic treatments or artificial light was given to the plants. Temperatures ranged from 15 to 25 degrees Celsius during the day and 10 to 18 degrees at night. Observation data was recorded in September of 2021.

Those skilled in the art will appreciate that certain characteristics will vary with older or, conversely, with younger plants. 'Florice' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 edition.

A botanical description of 'Florice' and a comparison with the parent plants and the most similar commercial *Fragaria* cultivar known to the inventor, is provided below.

Plant description:

*Growth habit*.—Acaulescent, stoloniferous perennial; with leaves and inflorescence developing from basal rosettes with approximately 6 rosettes per pot; no lateral branching is present.

*Plant profile*.—Flattened globular.

*Average height*.—20.5 cm to the top of the foliar plane; 28.2 cm to the top of the floral plane.

*Average width*.—75.0 cm.

*Plant vigor*.—Moderately vigorous.

*Rate of growth*.—Moderately fast growing.

*Propagation*.—Mode of propagation — Asexual propagation is accomplished by rooting stolon cuttings. Time to initiate roots — Rooting is initiated in approximately 10 days when grown with an ambient average temperature of 18 degrees Celsius. Time to produce a marketable rooted cutting — Approximately 35 days to produce a rooted cutting. Time to produce a marketable containerized plant — Approximately 9 months to produce a marketable plant in a 13 cm nursery container.

*Pest resistance and susceptibility*.—Excellent resistance to *Phytophthora cactorum* root rotting disease, but otherwise the claimed plant is not any more or less tolerant or susceptible to pests or diseases known to effect *Fragaria* x *ananassa*.

*Environmental tolerances*.—Adapt to USDA Zones 4 through 9 and temperatures ranging from at least minus −32 degrees Celsius to 40 degrees Celsius; low to moderate tolerance to rain; moderate to high tolerance to wind.

Root system:

*Type*.—Moderately fibrous root system, with adventitious rooting at stolon nodes.

*Branching*.—Very freely branched.

*Density*.—Moderately dense.

*Distribution*.—The majority of the root system is somewhat shallow.

*Diameter*.—Largest roots measuring 1.0 mm in diameter.

*Texture*.—Smooth; lacking root hairs.

*Color*.—White, RHS 155B.

Stolons:

*Attitude*.—Prostrate.

*Aspect*.—Rounded.

*Length*.—85.1 cm.

*Diameter*.—0.3 cm.

*Internode length*.—19.8 cm.

*Strength*.—Strong.

*Texture*.—Sparsely covered with short hairs; average length of hairs is 0.075 cm; colored translucent white, nearest to nearest to RHS NN155D.

*Luster*.—Matte.

*Color, immature stolons*.—Yellow-green, nearest to RHS 144A.

*Color, mature stolons*.—Yellow-green, nearest to RHS N144C.

*Color, immature stolons*.—Yellow-green, nearest to RHS N144C.

Foliage:

*Arrangement*.—Alternate.

*Attachment*.—Petiolate.

*Attitude*.—Upward and outward.

*Division*.—Trifoliate.

*Compound leaf outline*.—Reniform.

*Length*.—16.2 cm, excluding the petiole.

*Width*.—19.8 cm.

*Quantity*.—6 leaves per rosette.

*Leaflets*.—Quantity — 3. Shape — Varying from broad ovate to broad obovate to near orbicular. Length —11.0 cm. Width — 10.0 cm. Aspect — Slightly concave. Apex — Very abruptly acute. Base — Broadly attenuate. Margin — Coarsely serrate to crenate. Texture, adaxial surface — Slightly rugose and sparely covered with thin, soft hairs with an average length of 0.1 cm; hairs are a translucent white, nearest to nearest to RHS NN155D. Texture, abaxial surface — Slightly rugose and glabrous except for the veins which are moderately covered with very thin, soft adpressed hairs with an average length of 0.075 cm; hairs are a translucent white, nearest to nearest to white, nearest to RHS NN155D. Luster, adaxial surface — Very slightly glossy. Luster, abaxial surface — Matte. Color — Juvenile foliage color, adaxial surface — Green, nearest to RHS 143A. Juvenile foliage color, abaxial surface — Green, nearest to RHS 138B. Mature leaf color, adaxial surface — Nearest to a mixture of green and yellow-green, RHS NN137A and 147A yet closest to RHS NN137A. Mature leaf color, abaxial surface — Nearest to a mixture of green and greyed-green, RHS 138B and 191A. Venation — Type — Pinnate. Vein color, adaxial surface — Yellow-green, nearest to RHS 144A. Vein color, abaxial surface — Yellow-green, nearest to in between RHS N144D and 145A.

*Petiole*.—Length — 29.3 cm. Diameter — 0.4 cm. Strength — Strong. Texture, adaxial and abaxial surfaces — Sparsely to moderately covered with thin strigose hairs with an average length of 0.2 cm; hairs are a translucent white, nearest to RHS NN155D. Luster, adaxial and abaxial surfaces — Slightly glossy. Color, adaxial surface — Yellow-green, nearest to RHS 144A. Color, abaxial surface — Yellow-green, nearest to RHS 144A.

*Stipules*.—General — Two leafy stipules present at the base of each leaf. Shape — Narrow deltoid. Length — Average of 3.8 cm. Width — Average of 0.8 cm. Apex — Narrowly acute. Base — Broad cuneate. Aspect — Folded. Color, adaxial surface — Yellow-green, nearest to in between RHS 145A and 145B. Color, abaxial surface — Yellow-green, nearest to in between RHS 145A and 145B. Texture, adaxial surface — Glabrous. Texture, abaxial surface — Covered with soft hairs with an average length of 0.15 cm; hairs are a translucent white, nearest to RHS NN155D.

Inflorescence:

*Type*.—Compound cymose panicle, generally referred to as a truss.

*Natural flowering season*.—From spring into summer in Ens, Netherlands.

*Time to flower*.—9 months.

*Length*.—8.5 cm, including the peduncle.

*Diameter*.—5.9 cm.

*Quantity of open flowers per inflorescence*.—6.

*Quantity of buds per inflorescence*.—5.

*Quantity of flowers and buds per plant*.—100.

*Peduncle*.—Length — 16.1 cm. Diameter — 0.3 cm. Aspect — At an average angle of 70 degrees to horizontal. Strength — Moderately strong to strong. Texture — Densely covered with thin, soft hairs with an average length of 0.2 cm; hairs are a translucent white, nearest to RHS NN155D. Luster — Slightly glossy. Color — Yellow-green, nearest to RHS 144A.

Flower buds:

*Shape*.—Ovate.

*Length*.—Average of 1.0 cm.

*Diameter*.—Average of 0.9 cm.

*Texture*.—Smooth and glabrous with the exception of the immature sepals which are moderately covered with thin, soft hairs with an average length of 0.05 cm; hairs are a translucent green-white, nearest to RHS 157D.

*Luster*.—Matte.

*Color*.—Green-white, nearest to RHS 1578; immature sepals are green, nearest to RHS 138C.

Flower:

*Form*.—Rotate; single.

*Aspect*.—Upright and outward.

*Flower diameter*.—3.0 cm.

*Flower depth*.—1.5 cm.

*Fragrance*.—Moderately sweet fragrance.

*Flowering habit*.—Moderately free-flowering.

*Lastingness*.—Approximately 7 days.

*Persistent*.—Self-cleaning.

*Pedicels*.—Length — 4.1 cm. Diameter — 0.15 cm. Aspect — Upward; approximately 45 degrees to the peduncle axis. Strength — Moderately strong. Texture — Densely covered with thin, soft strigose hairs with an average length of 0.2 cm; hairs are a translucent white, nearest to RHS NN155D. Luster — Slightly glossy. Color — Yellow-green, nearest to RHS 144B.

*Petals*.—Arrangement — Rotate with a single whorl of free petals. Quantity of Petals — 5 and occasionally 6. Shape — Near orbicular. Length — 1.2 cm. Width — 1.2 cm. Apex — Obtuse. Base — Broad cuneate. Margin — Entire; slightly undulated. Aspect — Very slightly concave. Texture and luster of upper surface — Glabrous; moderately velvety; matte. Texture and luster of lower surface — Glabrous; moderately velvety; matte. Petal color when opening, upper surface — White, nearest to RHS NN155B. Petal color when opening, lower surface — White, nearest to RHS NN155B. Petal color when fully opened, upper surface — White, nearest to RHS NN155B. Petals do not fade with age. Petal color when fully opened, lower surface — White, nearest to RHS NN155B. Petals do not fade with age. Petal venation color, fully opened, upper surface — Veins are not visible. Petal venation color, fully opened, lower surface — Veins are not visible.

*Calyx*.—Shape — Rotate. Length — 1.0 cm. Diameter — 3.2 cm. Sepals — Arrangement — Rotate with sepals in a single whorl and fused at the base. Quantity — 12. Length — 1.4 cm. Width — 0.5 cm. Shape — Ovate to oblong. Apex — Varying from acute to trilobed with acute lobe apices. Base — Fused. Sepal lobe margin — Entire; not undulated. Texture, upper surface — Sparsely covered with thin, soft hairs with an average length of 0.075 cm; hairs are a translucent white, nearest to nearest to RHS NN155D. Texture, lower surface — Moderately covered with thin, soft hairs with an average length of 0.1 cm; hairs are a translucent green-white, nearest to nearest to 157D. Luster, adaxial surface — Matte. Luster, abaxial surface — Matte. Color when opening, upper surface — Green, nearest to RHS 137B. Color when opening, lower surface — Green, nearest to RHS 138B. Color when fully opened, upper surface — Green, nearest to in between RHS NN137A and NN137B; base is lighter, nearest to RHS 138A. Color when fully opened, lower surface — Green, nearest to RHS 138A.

*Bracts*.—Position — Two bracts are present at the base of each pedicel. Shape — Narrow elliptic to narrow ovate. Aspect — Carinate. Length — 2.5 cm. Width — 0.8 cm. Apex — Narrow acuminate. Base — Attenuate. Margins — Carinate. Color, adaxial surface — Green, nearest to RHS NN137B. Color, abaxial surface — Green, nearest to in between RHS 138A and 138B. Texture, adaxial surface — Sparsely covered with thin, soft hairs with an average length of 0.075 cm; colored a translucent white, nearest to nearest to RHS NN155D. Texture, abaxial surface — Moderately covered with thin, soft hairs with an average length of 0.1 cm; hairs are a translucent green-white, nearest to RHS 157D.

Reproductive organs:

*Stamens*.—Quantity — Approximately 25. Anthers — Attachment — Basifixed. Shape — Oblong. Length — 0.05 cm. Width — 0.05 cm. Color — Yellow-orange, nearest to RHS 14A. Filaments — Length — Approximately 0.2 cm. Color — Yellow-green, nearest to RHS 150B. Pollen, abundance — Sparse. Pollen, color — Yellow, nearest to in between RHS 13B and 13C.

*Pistil*.—Quantity — 150. Length — 0.1 cm. Style — Length — 0.09 cm. Color — Green-yellow, nearest to RHS 1B. Stigma — Shape — Club-shaped. Length — 0.03 cm. Diameter — 0.03 cm. Color — Yellow-green, nearest to RHS 153D.

*Ovary color*.—Yellow-green, nearest to RHS 145B.

Seed and fruit:

*Fruit*.—Harvest Season — July through September in the Netherlands. Time to maturity — Approximately 5 weeks after flowering. Quantity — An average of 100 per plant. Dimensions — 3.6 cm long and 3.9 cm in diameter. Weight — 17.0 grams, on average. Shape — Short conical. Texture — Moderately covered with very short, soft hairs with an average length of 0.04 cm; hairs are a translucent greyed-white, nearest to RHS 156D. Luster — Glossy. Color — Immature fruit — Yellow-green, nearest to RHS 145D yet lighter. Immature flesh — Green-white, nearest to RHS 157D. Mature fruit — Red, nearest to RHS 46A. Mature flesh — Red, nearest to RHS 46C. Fruit flavor — Sweet and slightly acidic. Firmness of flesh — Firm. Lastingness of fruit — Approximately 1 week. Market use — Fresh fruit market.

*Achenes*.—Position — Below the fruit surface. Quantity of achenes per fruit — Approximately 150. Shape — Flattened; outline is ovate. Length — 0.125 cm. Diameter — 0.08 cm. Texture — Smooth; glabrous. Color — Greyed-orange, nearest to in between RHS 164A and 164B.

COMPARISON WITH THE PARENTS

Plants of the new cultivar 'Florice' may be distinguished from its seed parent, *Fragaria* x *ananassa* '06-095-06' (unpatented), by the characteristics described in Table 1.

TABLE 1

| Characteristic | 'Florice' | '06-095-06' |
|---|---|---|
| Foliage abundance. | More abundant than '06-095-06'. | Less abundant than 'Florice'. |
| Quantity of stolons. | More than '06-095-06'. | Fewer than 'Florice'. |
| Position of achenes on the fruit. | Level with the fruit surface. | Above the fruit surface. |
| Fruit taste. | A pleasant blend of sweet and sour, with sweetness being the more dominant flavor. | A pleasant blend of sweet and sour, with sourness being the more dominant flavor. |

Plants of the new cultivar 'Florice' may be distinguished from its pollen parent, *Fragaria* x *ananassa* '00-113-13' (not patented), by the characteristics described in Table 2.

TABLE 2

| Characteristic | 'Florice' | '00-113-13' |
|---|---|---|
| Foliage abundance. | More abundant than '00-113-13'. | Less abundant than 'Florice'. |
| Quantity of stolons. | More than '00-113-13'. | Fewer than 'Florice'. |
| Position of achenes on the fruit. | Level with the fruit surface. | Above the fruit surface. |
| Fruit taste. | A pleasant blend of sweet and sour, with sweetness being the more dominant flavor. | A pleasant blend of sweet and sour, with sourness being the more dominant flavor. |

COMPARISON WITH THE CLOSEST KNOWN COMMERCIAL COMPARATOR

Plants of the new cultivar 'Florice' may be distinguished from the most similar known commercial comparator, *Fragaria* x *ananassa* 'Florin Florentina' (Community Plant Variety Rights grant number 40665), by the characteristics described in Table 3.

TABLE 3

| Characteristic | 'Florice' | 'Florin Florentina' |
|---|---|---|
| Foliage abundance. | More abundant than 'Florin Florentina'. | Less abundant than 'Florice'. |
| Quantity of stolons. | More than 'Florin Florentina'. | Fewer than 'Florice'. |
| Position of achenes on the fruit. | Level with the fruit surface. | Above the fruit surface. |
| Fruit taste. | A pleasant blend of sweet and sour, with sweetness being the more dominant flavor. | A pleasant blend of sweet and sour, with sourness being the more dominant flavor. |

That which is claimed is:

1. A new and distinct cultivar of *Fragaria* x *ananassa* plant named 'Florice', substantially as described and illustrated herein.

* * * * *